United States Patent
Birnbach

(10) Patent No.: US 7,978,823 B2
(45) Date of Patent: Jul. 12, 2011

(54) CASCADE VOLTAGE AMPLIFIER AND METHOD OF ACTIVATING CASCADED ELECTRON TUBES

(75) Inventor: Curtis A. Birnbach, New Rochelle, NY (US)

(73) Assignee: Advanced Fusion Systems LLC, Newton, CT (US)

( * ) Notice: Subject to any disclaimer, the term of this patent is extended or adjusted under 35 U.S.C. 154(b) by 0 days.

(21) Appl. No.: 12/619,407

(22) Filed: Nov. 16, 2009

(65) Prior Publication Data
US 2010/0289577 A1 Nov. 18, 2010

Related U.S. Application Data

(63) Continuation-in-part of application No. 12/467,974, filed on May 18, 2009.

(51) Int. Cl.
*H05G 1/32* (2006.01)
(52) U.S. Cl. ........................ 378/111; 378/122
(58) Field of Classification Search .................. 378/101, 378/105, 106, 111, 122
See application file for complete search history.

(56) References Cited

U.S. PATENT DOCUMENTS

| | | | |
|---|---|---|---|
| 2,478,446 | A | 8/1949 | Alfven |
| 4,950,962 | A | 8/1990 | Bimbach et al. |
| 5,030,921 | A | 7/1991 | Kane |
| 5,757,115 | A | 5/1998 | Narita et al. |
| 7,345,537 | B2 | 3/2008 | Apel et al. |
| 2006/0018085 | A1 | 1/2006 | Kelly |

OTHER PUBLICATIONS

Bellau, RV et al, Activation of a multi-emitter silicon carbide p-n junction cold cathode, J. Phys. D: Appl. Phys., Dec. 1971, 2022-2030.
Florio, JV et al, Studies of Electron Tube Mats.&Thermionic Emission Processes, Sep. 30, 1962, http://oai.dtic.mil/oai/oai?verb=getRecord&metadataPrefix=html&identifier=AD0413928>.
General Electric Co., A Study of Films in Electron Tubes, May 1, 1961, <http://oai.dtic.mil/oai/oai?verb=getRecord&metadataPrefix=html&identifier=AD0278095>.
Doucette Assoc. Inc., Quant. Study of Evolution of Gases Electron Tubes & Mats., Dec. 18, 1962, <http://oai.dtic.mil/oai/oai?verb=getRecord&metadataPrefix=html&identifier=AD0403984>.

*Primary Examiner* — Jurie Yun
(74) *Attorney, Agent, or Firm* — Bruzga & Associates; Charles E. Bruzga

(57) ABSTRACT

Disclosed is a cascade voltage amplifier for producing an amplified output in pulse or continuous wave form comprises at least one non-final stage with an electron tube configured as a switching and Class A or C amplifying structure. A final stage comprises an electron tube configured as a Class A or C amplifying structure. The at least one non-final stage and the final stage are connected in series, and the amplified output has a voltage of at least 1000 volts. Further disclosed is a method of activating a plurality of cascaded electron tube stages within a common vacuum enclosure. Beneficially, a sufficient amount of energy supplied to the first stage serially propagates through any intervening stage to the final stage so as to facilitate activation of all tube stages.

21 Claims, 8 Drawing Sheets

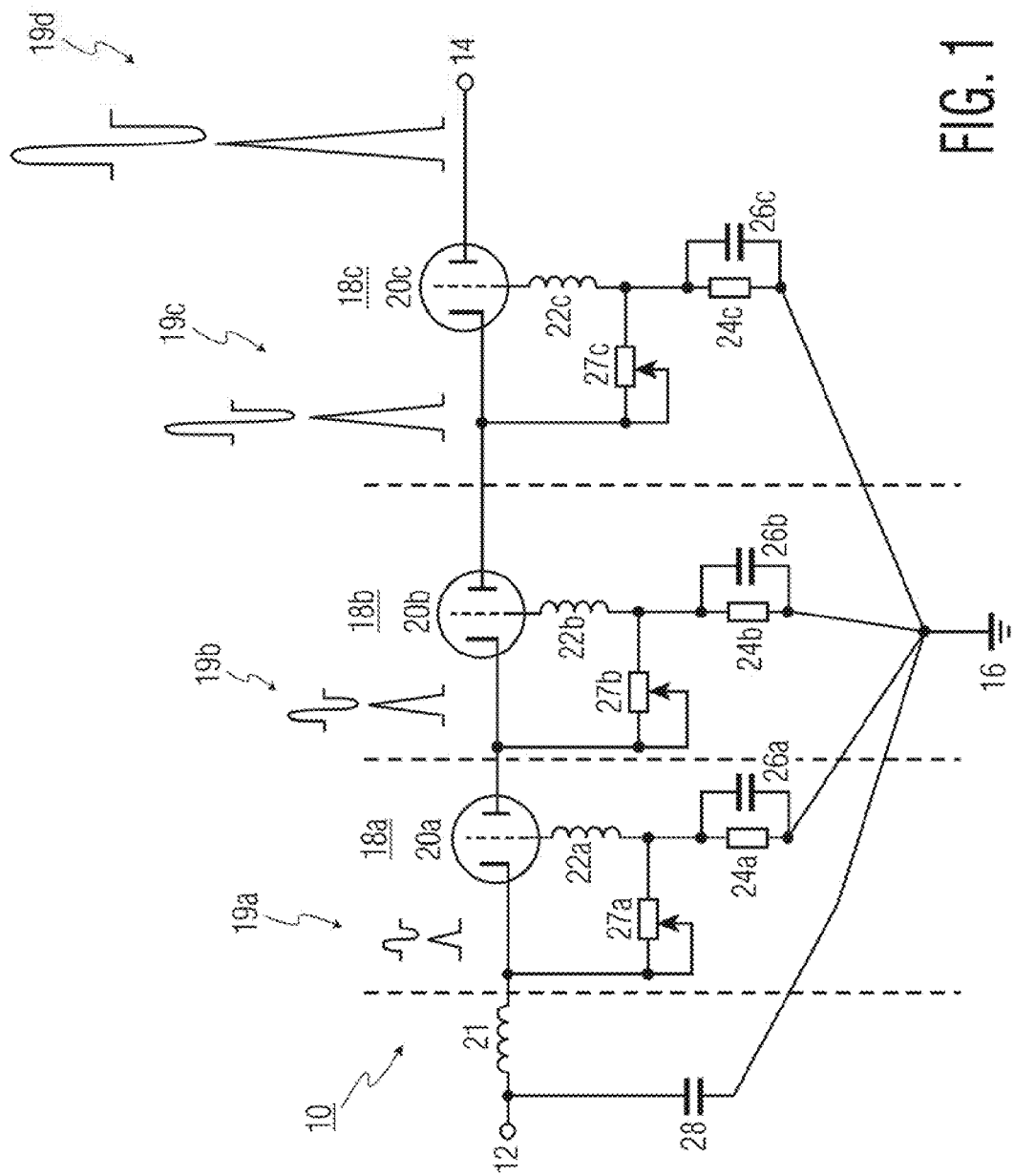

ized into a load via a high voltage switch, such as a spark gap or hydrogen thyratron. While PFN's usually consist of a series of high voltage energy storage capacitors and inductors, they can also consist of just one or more capacitors. These components are interconnected as a "ladder network" that behaves similarly to a length of transmission line. Upon command, a high voltage switch then transfers the energy stored within the PFN into the load. When the switch "fires" (closes), the network of capacitors and inductors within the PFN creates a nominally square output pulse of short duration and high power. This high power pulse becomes a brief source of high voltage to the load. In most pulse modulator circuits, a specially-designed pulse transformer is connected between the PFN and load to improve the impedance match between the PFN and the load, so as to improve power transfer efficiency. A pulse transformer such as this is typically required when driving higher-impedance devices such as klystrons or magnetrons from a PFN. Because a PFN is charged over a relatively long time and then discharged over a very short time, the output pulse may have a peak power of megawatts.

CASCADE VOLTAGE AMPLIFIER AND METHOD OF ACTIVATING CASCADED ELECTRON TUBES

FIELD OF THE INVENTION

The invention relates to a Class A or Class C cascade voltage amplifier for producing an amplified output in pulse or continuous form. It also relates to a method of activating a plurality of electron tube stages in cascaded structure.

BACKGROUND OF THE INVENTION

The production of high-energy high-voltage pulses is a fundamental requirement for many modern electronic applications. Prior art circuits for achieving pulses of this type include:
1. Cockcroft-Walton voltage multiplier
2. Marx Generators
3. Pulse Modulators All of the foregoing prior art circuits have problems over which improvement would be desirable.

The Cockcroft-Walton voltage multiplier is the simplest type of voltage multiplier. First built in 1932 by Cockcroft and Walton for nuclear physics experiments. It is formed from a voltage multiplier ladder network of capacitors and diodes to generate high voltages. Unlike transformers, a Cockcroft-Walton voltage multiplier does not use an iron core transformer. Using only an oscillator, capacitors and diodes, these voltage multipliers can step up relatively low voltages to extremely high values, while at the same time being far lighter and cheaper than transformers. In such voltage multipliers, the voltage across each stage of the cascade is equal to only twice the peak input voltage, whereby it has the advantage of using relatively low cost components.

The Cockcroft-Walton voltage multiplier has a number of drawbacks, however. As the number of stages is increased, the voltages of the higher stages begin to 'sag', primarily due to the AC impedance of the capacitors in the lower stages. When supplying an output current, the voltage ripple rapidly increases as the number of stages is increased. For these reasons, Cockcroft-Walton voltage multipliers with large number of stages are typically used only where relatively low output current Is required. It would therefore be desirable to provide a circuit for achieving a high voltage pulse that avoids such drawbacks.

The Marx Generator is a more advanced type of voltage-multiplication circuit that relies on charging a plurality of capacitors in parallel and then discharging them in series. The parallel-series switching operation is usually accomplished using spark gaps as switches. It is extensively used for simulating the effects of lightning during high voltage and aviation-equipment testing. The spark gaps are placed as close as possible together for maximum ultraviolet (UV) light exchange between them (emitted by the arcs) for minimum jitter.

Among the drawbacks of the well-known Marx generator is that it suffers from reliability problems due to wear in the spark gap switches, causing irregular operation and increase in the amount of jitter. These problems are a serious disadvantage. It would be desirable to provide a circuit for achieving a high voltage pulse that avoids the foregoing reliability and jitter problems.

A third prior art circuit for generating high voltage pulses is known as a pulse modulator. It was originally developed during the Second World War as power supplies for radar systems. The pulse modulator incorporate a Pulse Forming Network (PFN), which accumulates electrical energy over a comparatively long time, and then releases the stored energy in the form of a nominally-square pulse of comparatively short duration, for various pulsed power applications. In practice, a PFN is charged by means of a high voltage power source, then rapidly discharged Pulse modulators are limited by the requirement for a pulse transformer, which is slow, bulky and subject to saturation. It would be desirable to provide a circuit for achieving a high voltage pulse that avoids such drawbacks.

It is also known in the prior art that Class A amplifiers can be cascaded for use with continuous wave (e.g., sinusoidal) RF signals. However, such prior art cascaded amplifiers have the drawbacks of being bulky and inefficient. It would be desirable to provide cascaded Class A amplifiers that are smaller and more efficient.

Activation of electron tubes is the process by which the cathode is converted from its as-manufactured state into a functioning electron emitter. Typically, this process involves drawing current from the cathode through the anode, while the tube is still connected to a vacuum pumping system. Specific implementation varies with the type of cathode used. Activation requires supplying operating voltages equal to or greater than those normally encountered in operation of the tube. Activation takes place while the tube is still connected to an external vacuum pump system. This is done to facilitate the removal of impurities released from the cathode by the activation process. In the case of very high voltage tubes, the cost of suitable power supplies is very high. It would, therefore, be desirable to minimize the cost of high voltage power supplies and to simplify and expedite the manufacturing process.

BRIEF SUMMARY OF THE INVENTION

One form of the invention provides a cascade voltage amplifier for producing an amplified output in pulse or continuous wave form. The amplifier comprises at least one non-final stage with an electron tube configured as a switching and Class A or C amplifying means. A final stage comprises an electron tube configured as a Class A or C amplifying means. The at least one non-final stage and the final stage are connected in series, and the amplified output has a voltage of at least 1000 volts.

The foregoing cascade voltage amplifier avoids the drawbacks of Cockcroft-Walton voltage multiplier of voltage ripple when supplying an output current with several stages. It also avoids the reliability and jitter problems of Marx generators. It further avoids the drawbacks of pulse modulators relating to inclusion of a slow and bulky pulse transformer and its susceptibility to saturation.

Another form of the invention provides a method of activating a plurality of cascaded electron tube stages within a common vacuum enclosure. The method comprises interconnecting the plurality of cascaded electron tube stages in series, from a non-final stage to a final stage, in such a manner that in each non-final stage an electrode is connected to an electrode of a subsequent stage by a respective electrical interconnection line. At least one of said respective electrical connection line comprises a linking structure for electrically and mechanically joining an electrode of a previous stage with an electrode of a subsequent stage. The plurality of cascaded electron tube stages is placed within the vacuum enclosure and air is exhausted from the enclosure. An electrical voltage is provided between cathode and anode of a first serially-connected stage so as to supply electrical energy to the first stage. A sufficient amount of said energy serially propagates through any intervening stage to the final stage so as to facilitate activation of all tube stages.

The foregoing method avoids the drawbacks of the prior art method of activating individual tubes mentioned above. This is accomplished by using, in a preferred form, only a single power supply to activate all the stages cascaded electron tube stages nearly simultaneously. The power supply needs to only meet the voltage requirement of the first stage tube, since the increased voltage required for each succeeding stage is provided by the voltage gain of the preceding stage. This avoids the need for larger and more costly power supplies for the succeeding stages, and for larger and substantially more complex exhaust stations involving, for instance, the use of larger feedthroughs that then require a larger vacuum enclosure and increased vacuum pumping and heating requirements.

BRIEF DESCRIPTION OF DRAWINGS

In the drawings, in which like reference numerals refer to like parts:

FIG. 1 shows a schematic diagram of a cascade voltage amplifier for providing amplified output in pulse or continuous wave form, in accordance with an aspect of the invention;

DETAILED DESCRIPTION OF THE INVENTION

Figure 2A:
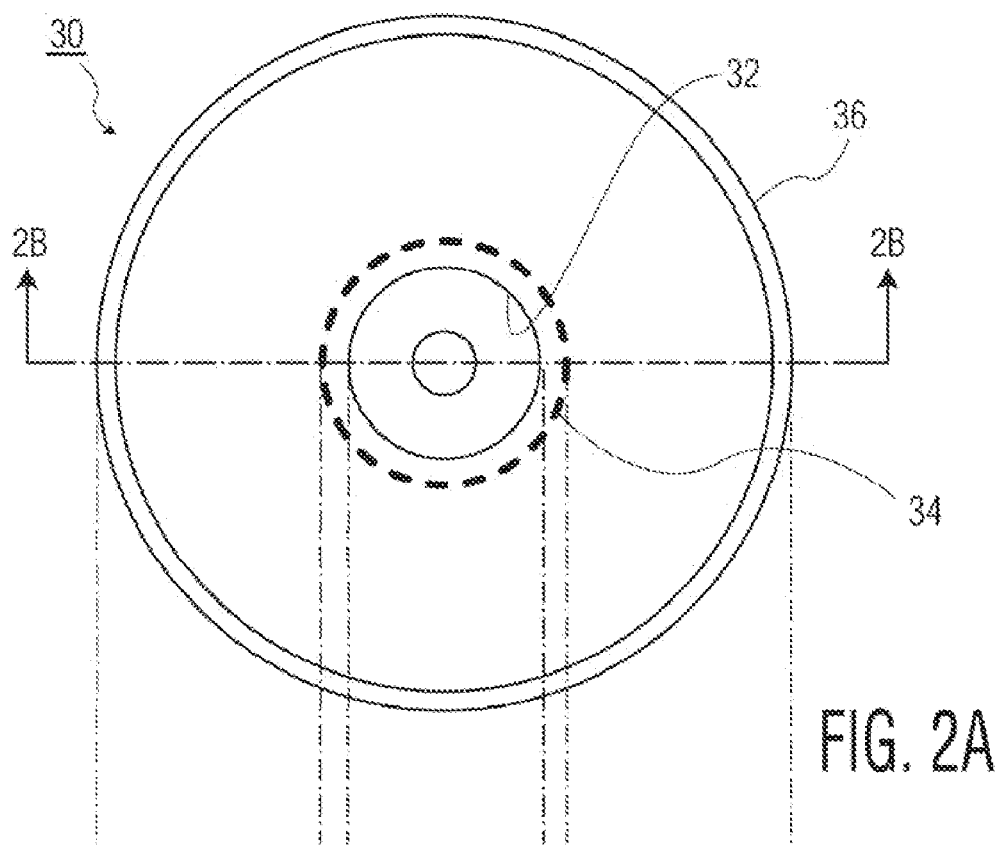
FIGS. 2A and 2B show simplified top plan and associated cross-sectional views of a high-voltage cold-cathode field emissions triode that may be used in the invention, with FIG. 2B being taken at arrows 2B-2B in FIG. 2A.

This description describes the three topics of (1) circuit topology, (2) preferred circuit implementation, and (3) method of activating cascaded electron tubes.

1. Circuit Topology

FIG. 1 shows a cascade voltage amplifier (CVA) 10 configured as a switching, and as a modified Class A amplifier, circuit. Class A amplifier operation is described below. CVA 10 includes input 12 and output 14 terminals and an earth ground 16 in accordance with good RF design practice. For the purposes of the following description, CVA 10 is designed to provide output in excess of 1000 volts.

The particular version of CVA 10 shown consists of three stages 18a, 18b and 18c. The first stage 18a includes a cold cathode field emission tube 20a of triode configuration and has a grid biased to a standoff condition by a resistor 27a, which is preferably variable. An inductor 21, known as an anti-kickback choke, blocks reverse pulses and keeps them from reaching a negative high voltage capacitor 28 and charging a power supply (not shown) connected to input terminal 12. A blocking diode (not shown) can augment this function. A resistor 24a and capacitor 26a form an RC network to set a time constant to support, the conduction of the tube 20a.

In operation, an energy storage capacitor 28 becomes charged from voltage between input terminal 12 and RF ground 16. Cold-cathode field-emission triode electron tube 20a in conjunction with inductor 22a, resistor 24a, capacitor 26a and variable resistor 27a perform dual functions. These electron tubes are used to both form a pulse and to amplify it by anywhere from 3 dB to 10 dB, depending on the gain of the tube 20a as manufactured. Waveform pairs 19a, 19b, 19c and 19d illustrate gain of each stage of CVA 10. In each waveform pair 19a-19d, the upper waveform represents a sinusoidal signal, which is one mode of operation for CVA 10, and the lower waveform represents a pulse signal, which is another mode of operation. Waveform pair 19a represents the input to the CVA 10; pair 19b represents the output of the $1^{st}$ stage feeding the input of the $2^{nd}$ stage; pair 19c represents the output of the $2^{nd}$ stage feeding the input of the final stage; and pair 19d represents the output of the CVA 10.

Subsequent stages 18b and 18c are similar in function to above-described stage 18a and each is configured to operate as a Class A amplifier circuit. The key differences are in the voltage ratings of the different stages. The voltage ratings of the components of the CVA 10 must be commensurate with the voltages anticipated in each stage of the amplifier. Similarly, the tubes 18b and 18c are progressively larger in size to accommodate the increasing voltage.

All stages of the circuit are connected to a common RF ground 16 in accordance with good RF design practice.

It is noted that it is possible to reach higher voltages by adding additional stages in series with the main circuit. Care must be taken to ensure that the voltage ratings and insulation specifications are commensurate with the voltages to be encountered. The principal dimensions of each stage increase in a linear fashion to accommodate the higher voltage without arcing. Principal dimensions include interelectrode spacings and length and diameter of electrodes. A consequence of using more than two stages is that the risetime of the CVA 10 degrades as the number of stages increases.

It is not uncommon to put a circuit of this type in an insulating-oil tank or in a high pressure insulating-gas tank for higher reliability. Suitable transformer insulating oils are Shell Diala AX Shell Oil Company of Houston Tex., or equivalent. Suitable transformer insulating gas is Sulfur Hexafluoride ($SF_6$) available from Air Products and Chemicals, Inc. of Allentown, Pa., or equivalent.

With regard to the performance of the cold cathode field emission tubes of triode configuration, it is possible to control the over-gain of the CVA by setting the gain of each stage during manufacture of the tubes themselves. For the CVA circuit, individual tube gains in the range of 3 dB to 10 dB provide extremely stable operation. The tubes may be manufactured to have individual gains as high as 20 dB but it is difficult to keep the circuit from oscillating or ringing. This may be overcome by careful circuit design but this increases the component count and causes a commensurate decrease in maximum risetime as a result of increased circuit inductance.

Cold cathode field emission tubes $20a$, $20b$ and $20c$ are shown as directly connected in series with each other, but direct serial connection is not always desired. For instance, intermediate circuit elements such as inductance can be interposed between tubes $20a$, $20b$ and $20c$. For instance, adding inductances between stages results in longer pulses that have application in radar, medical imaging, lithotripsy, etc. One way to add inductance is to place a hollow ferrite choke (not shown) over the electrical interconnection between stages of the CVA 10. This is electrically equivalent to inserting a conventional inductor in the circuit at the same point.

Details of Class A operation of the stages $18a$-$18c$ of CVA 10 of FIG. 1 are as follows. Class A amplifiers are biased so that variations in input signal polarities occur within the limits of cutoff and saturation. With a triode electron tube, for example, if the grid becomes positive with respect to the cathode, electrons will be repelled by the grid and no current can flow in the anode circuit. This condition is known as cutoff. Saturation occurs when the grid becomes so negative with respect to the emitter that changes in the signal are not reflected in anode-current flow.

Biasing an amplifier in this manner places the DC operating point between cutoff and saturation and allows anode current to flow during the complete cycle (360 degrees) of the input signal, thus providing an output which is a replica of the input. The output from this amplifier is 180 degrees out of phase with the input, the output current still flows for the complete duration of the input.

Class A amplifiers are not considered high efficiency circuits when used in continuous wave (CW) typically sinusoidal circuits. The Class A amplifier is noted for its highly accurate amplification of the input signal. When used in ultra-short pulse amplification, as is found in the current invention, the efficiency increases. This is due to the difference between CW and pulse operation. In CW operation, the output stage is in continuous conduction, and as a result, the circuit draws power continuously. In ultra-short pulse operation, the situation is different. The output stages are only in conduction during the period of time that the pulse is present, and as a result, the circuit efficiency is very high. In broadband ultra-short pulse designs, DC coupled operation is practical without the need for large capacitors commonly found in this type of circuit. As used herein, an ultra-short pulse is one that has a risetime approximately in excess of 10-20 nanoseconds.

The combination of characteristics of the foregoing paragraph makes the Class A amplifier uniquely well-suited for pulse amplification applications. Historically, it has been used in radar circuits, but pulses in those circuits are substantially longer than the pulses contemplated by the current invention.

In addition to using cold cathode field emission techniques with a CVA, it is possible to implement the CVA using electron tubes with thermionic cathodes and filamentary electron sources. Use of this type of electron tube places significant limitations on the performance of the circuit, primarily in terms of current handling and overall voltage handling specifications.

Whereas the foregoing description has referred to creation of high voltage pulses, it is possible to operate the cascade voltage amplifier on continuous (e.g., sinusoidal) signals. In this way, continuous high gain output signals can be achieved in a compact and efficient manner.

2. Preferred Circuit Implementation

Figure 2B:
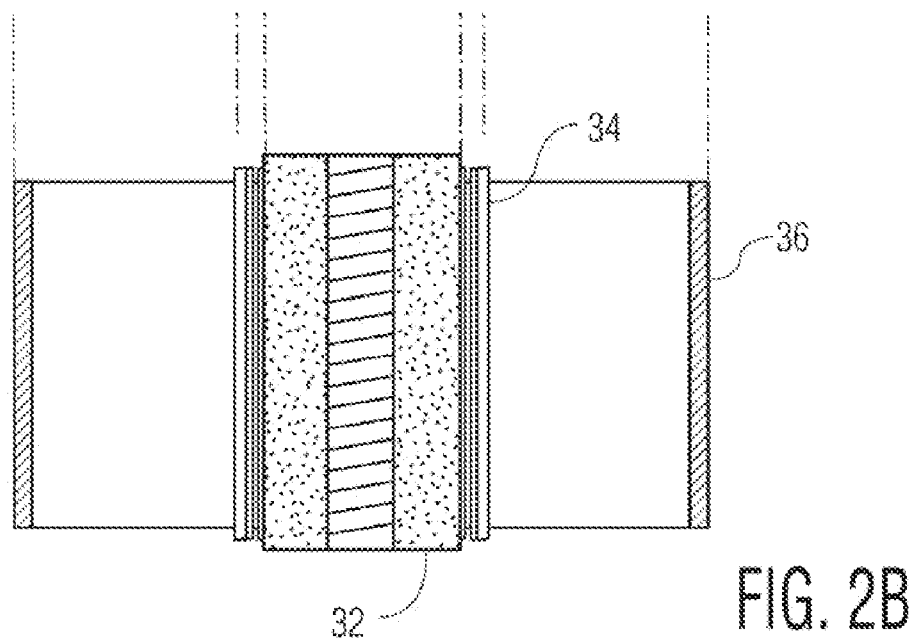

FIGS. 2A and 2B show basic structure of a high-voltage cold cathode field emission triode 30 that is preferably used to implement cold cathode field emission tubes $20a$-$20c$ in the circuit of FIG. 1. Triode 30 is also known as a Pulsatron, as described in U.S. Pat. No. 4,950,962 by the current inventor and others. The Pulsatron is scaled in size to operate in the continuous mode at a desired voltage. Triode 30 includes a cylindrically shaped cathode 32 which is encircled by a cylindrically shaped grid 34, which in turn is encircled by a cylindrically shaped anode 36. Grid 34 is shown as dashed lines to indicate that it would have suitable holes for passage therethrough of electrons. The anode 36, grid 34 and cathode 32 share a common main axis (not shown). The radial spacing from cathode 32 to grid 34 is such as to create therebetween a circular waveguide supporting the transverse electromagnetic mode (TEM). In FIGS. 2A and 2B, the cathode 32 is comprised of a graphite material, the grid 34 is comprised of a conductive metal such as nickel alloy, and the anode 36 is comprised of a refractory metal such as tungsten, by way of example.

Figure 2C:
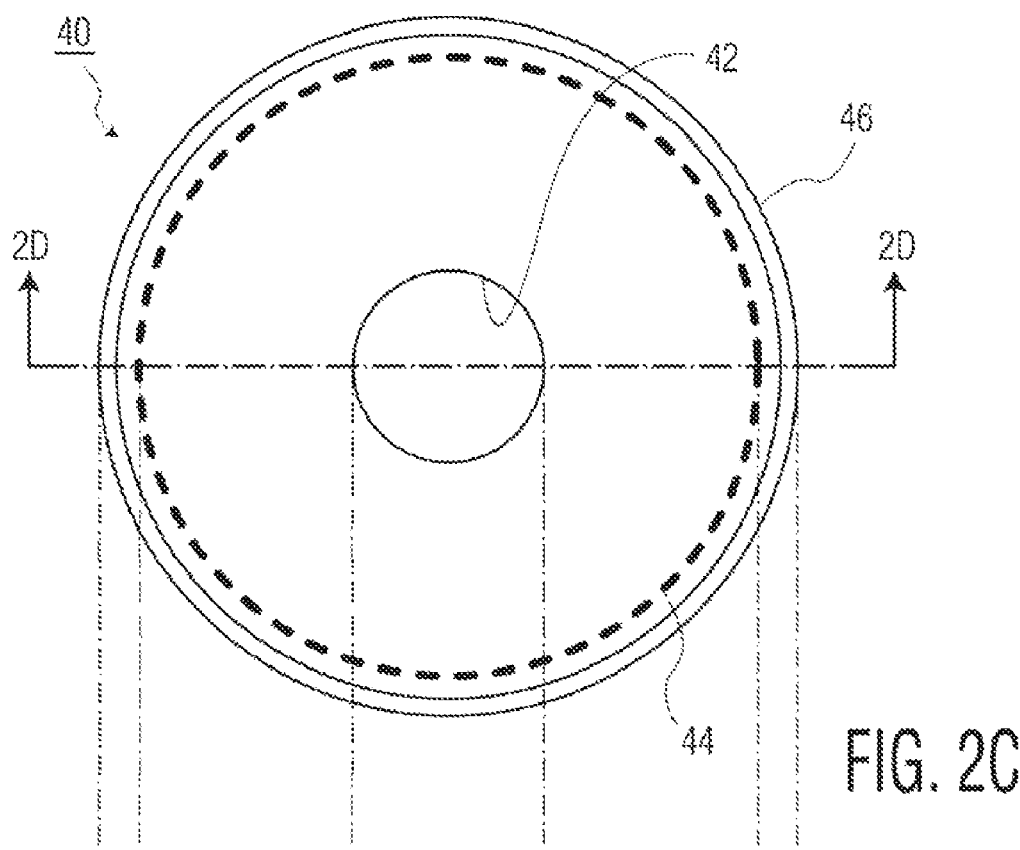
FIGS. 2C and 2D show similar views to FIGS. 2A and 2B, but for a modified high-voltage cold-cathode field-emission electron tube that may be used in the invention, with FIG. 2D being taken at arrows 2D-2D in FIG. 2C.
Figure 2D:
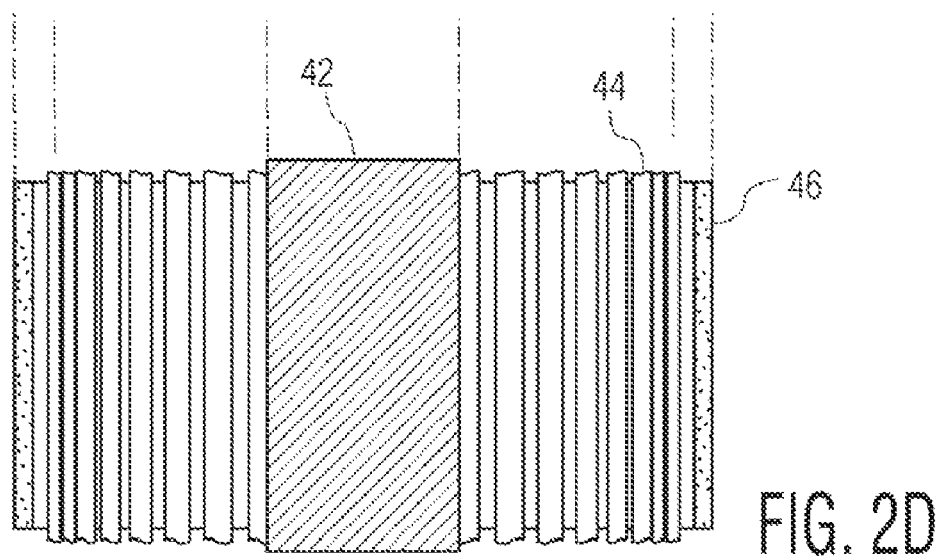

FIGS. 2C and 2D shows basic structure of another high-voltage cold-cathode field emission triode 40 of FIG. 2C that may implement cold cathode field emission tubes $20a$-$20c$ in the circuit of FIG. 1. Such a triode is also known is also known as a Pulsatron, as described in U.S. Pat. No. 4,950,962 by the current inventor and others. Triode 40 includes a cylindrically shaped anode 42. Encircling anode 42 is a cylindrically shaped grid 44, which is then encircled by a cylindrically shaped hollow cathode 46. Grid 44 is shown as dashed lines to indicate that it would have suitable holes for passage therethrough of electrons. The anode 42 and cathode 46 and grid 44 share a common main axis (not shown). The radial spacing from cathode 46 to grid 44 is such as to create therebetween a circular waveguide supporting the transverse electromagnetic mode (TEM). In FIGS. 2C and 2D, the cathode 46 is comprised of a graphite material and the anode 42 and grid 44 are comprised of a conductive metal such as high nickel alloys, by way of example.

There are several critical conditions that must be met when designing a grid for a cold cathode field-emission electron tube. They are:
(1) The grid-cathode or grid-anode spacing must be constant across the length of the grid. This is usually accomplished by placing the grid under high tension or building it with a rigid structure.
(2) The number of elements in the grid must be high enough to ensure a constant and uniform electric field in the grid-cathode or grid-anode region.
(3) There must be no sharp edges of burrs anywhere in the grid structure. Rather, individual elements can be round, flat or high aspect-ratio elliptical shapes. All edges must be fully radiused. In this context, fully radiused means that the edge in question has a radius equal to half the thickness of the material.

The actual implementation of these design rules is determined by the size of the grid being built.

Figure 3:
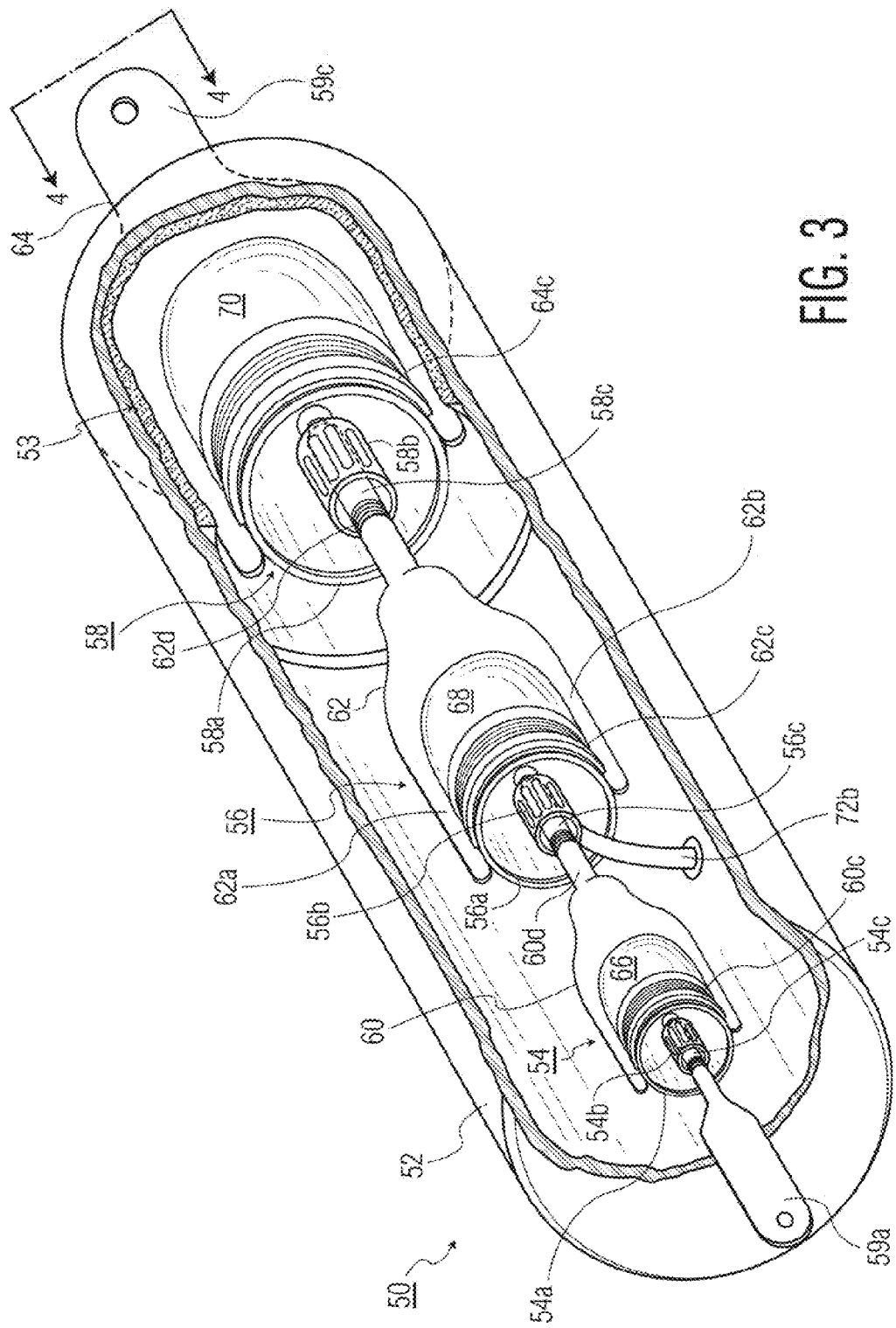
FIG. 3 is a simplified perspective view, partially cut away, of key parts of an integrated, three-stage cascade voltage amplifier, with various parts omitted for clarity, in accordance with an aspect of the invention.
Figure 4:
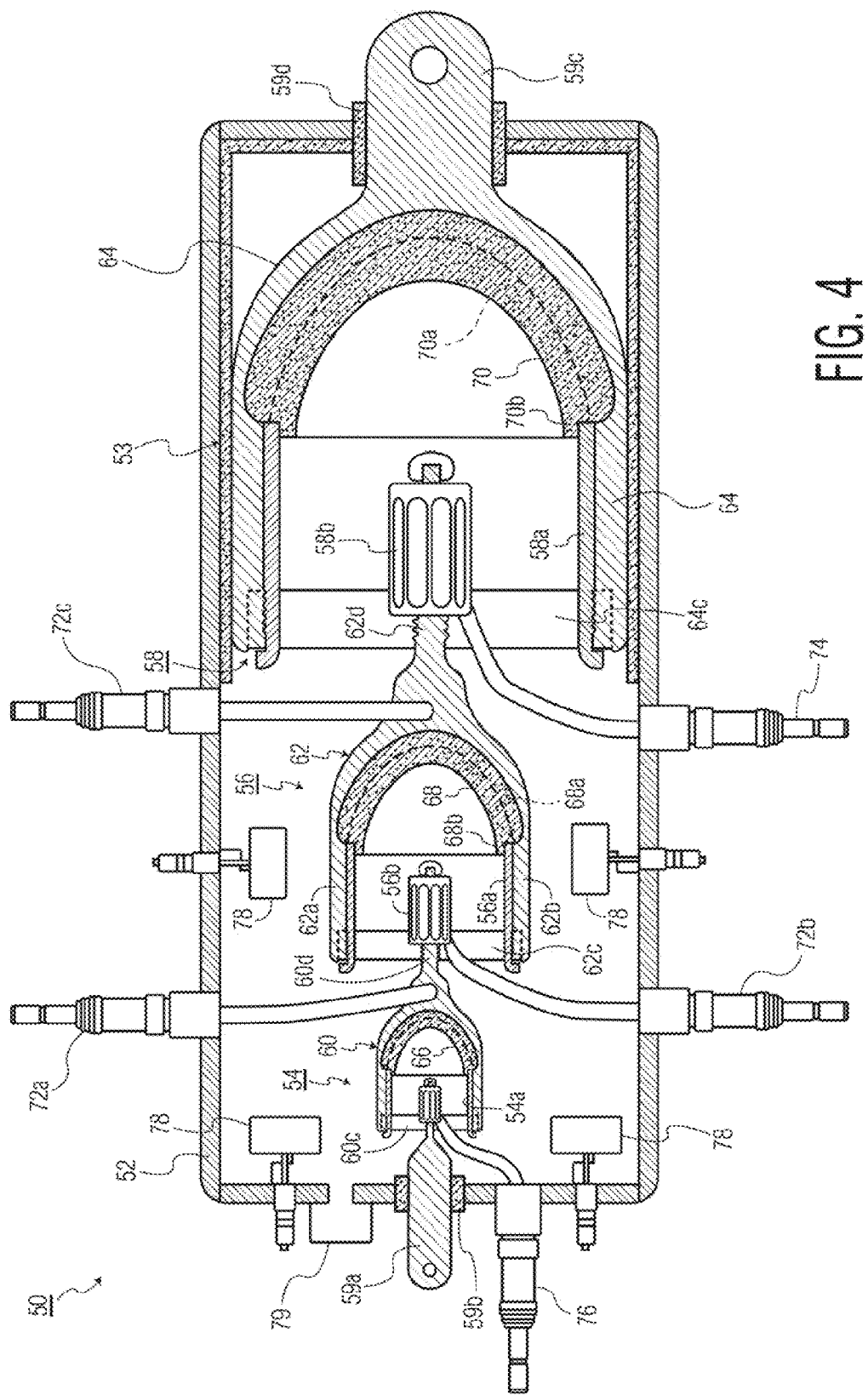
FIG. 4 is a simplified side plan view, partially in cross section, of the key parts of a cascade voltage amplifier of FIG. 3, taken at arrows 4-4 in FIG. 3, with various parts omitted for clarity.

FIGS. 3 and 4 show key parts of a cascade voltage amplifier (CVA) 50 in accordance with an aspect of the invention. With reference to both figures, a vacuum enclosure 52 of nickel alloy, for instance, encloses non-final stages 54 and 56 and final stage 58 of amplifier 50. As best shown in FIG. 4, CVA 50 includes first stage cathode input 59a and associated insulator 59b, and last stage anode output 59c and associated insulator portion 59d of dielectric insulator 53.

Advantages of using a common vacuum enclosure 52 for all three stages include manufacturing efficiency, compact size, and lower cost. However, there are some situations where it is not desirable, necessary or useful to place the electron tubes within a common vacuum enclosure. Conditions that would warrant the exclusion of a common vacuum enclosure include but are not limited to: circuits where fast risetime is not a consideration, circuits where extremely high voltages are developed which would necessitate a very large enclosure, circuits where a linear layout is not desirable, and prototype circuits.

Non-final stage 56 includes an anode 56a, a grid 56b and an internally threaded cathode 56c, which may conform to anode 36, grid 34 and internally threaded cathode 32 in FIGS. 2A and 2B. A non-final linking structure 62 supports the anode 56a of non-final stage 56, as well as supports the cathode 58c of subsequent stage 58. The linking structure 62 generally has the form of a two-tined fork on one end, with both tines 62a and 62b being visible in FIG. 4, and a cathode support 62d in the shape of a threaded pin for mounting the cathode, and an electrically conductive and refractory hemisphere 62e for retaining the cathode on the threaded pin 62d most easily seen in FIG. 5. Conductive and refractory hemisphere 62e has a second function of inhibiting end emission off the cathode. In an alternative integrated CVA that uses the cathode 46, grid 44 and anode 42 of FIGS. 2C and 2D, the centrally located anode 42 may be gaplessly integrated into linking structure 62. This can be realized by casting the linking structure 62 and the anode 42 as one piece, rather than assembling the linking structure by welding individual components together.

At one axial end of the linking structure 62 (along the axis of cathode 56c), linking structure 62 is connected to a ring 62c, preferably from being cast as one piece in a mold to near net shape and subsequently machined to final dimensions. Casting as one piece beneficially results in output signals bearing high fidelity to input signals and high speed operation. Alternative methods of construction include machining from bulk material or assembly from machined parts, which usually requires welding with resulting surface defects and non-uniformities that must be machined away.

Ring 62c has internal threads of typically 35 per centimeter, into which the anode 56a is screwed. The right-hand end of linking structure 62 terminates in a cathode support 62d for final stage 58. Preferably, linking structure 62 including ring 62c and cathode support 62d form an integral and gaplessly continuous structure, as results from being formed as one piece in a mold. The linking structure 62, including ring 62c and cathode support structure 62d are preferably formed of nickel alloy. Preferably, the linking structure 62 is an electrical transmission line over its entire length. This means that the transmission line portion of the linking structure 62 is greater than $1/10$ of the wavelength of the pulse. At this length the phase delay and the interference of any reflections on the line become important and can lead to unpredictable behavior in systems which have not been carefully designed using transmission line theory.

As shown best in FIG. 4, a ceramic insulator 68 of generally hemispherical shape has a rightward facing groove 68a for receiving a convex region of the linking structure 62, and has a lip 68b for overlying the inner periphery of the right hand end of the anode 56a.

Referring to FIGS. 3 and 4, electrical connections to non-final stage 56 through vacuum enclosure 52 are made by: intermediate feedthrough 72a, connected to cathode 56c (FIG. 3) of stage 56 (and also to anode 54a of stage 54); grid feedthrough 72b and intermediate feedthrough 72c connected to anode 56a of stage 56 (and also cathode 58c of stage 58). A grid feedthrough 74 allows electrical access to the grid 58b of final stage 58, and a grid feedthrough 76 allows electrical access to grid 54b (FIG. 3). Chemical getter pumps 78 and associated feedthroughs are also shown in FIG. 4. As is customary, all feedthroughs are vacuum-sealed and electrically insulated with dielectric material. The integrated CVA 10 includes other features common to all vacuum tubes, such as an exhaust tubulation 79, and may include an active vacuum pump if desired.

FIG. 3 omits various elements for clarity, for instance, showing only grid feedthrough 72b rather than all the feedthroughs shown in FIG. 4. Further omitted for clarity from FIGS. 3 and 4 are dielectric support elements for accurate positioning and supporting the various internal tube elements. Inclusion of such support elements will be routine to those of ordinary skill in the art.

Figure 5:
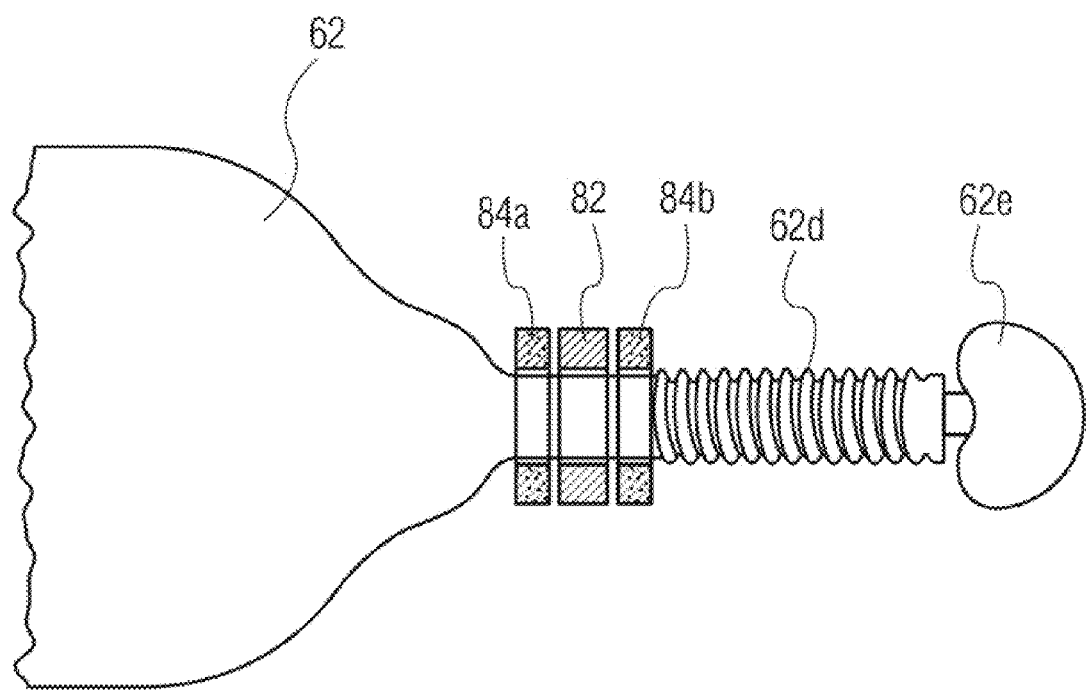
FIG. 5 is detail side plan view of a linking structure shown in FIGS. 3 and 4, together with an added inter-stage ferrite choke.

Normally, the risetime of CVA 10 is determined solely by risetime of the final stage 58. However, in circuit applications where it is desirable to deliberately slow down or extend the pulse width of an input pulse, it is possible to place a ferrite choke on the interconnecting transmission line element. For instance, as shown in FIG. 5, a ferrite choke 82 interposed between a pair 84a, 84b could be placed on cathode support structure 62d. Further details of a ferrite choke are as follows.

A ferrite choke is a non-resistive electronic circuit element which is composed of ferromagnetic compounds that contain iron and trace amounts of nickel, zinc, or manganese oxides. The impedance properties of the ferrite choke allow it to act with a high resistance to high frequency signals and low resistance to lower frequency signals. In this way, the high frequency noise is suppressed and the absorbed energy is converted to a very small amount of heat. The type of ferrite material used in the bead will determine the frequency of operation, and the physical dimensions and shape of the ferrite choke determine the amount of pulse modification possible.

It is possible to use the integrated cascade voltage amplifier 50 (FIGS. 3-4) in a Class C amplifier circuit, as well as in a Class A amplifier circuit.

The foregoing description of FIGS. 3 and 4 has focused on the second non-final stage 56. The first stage 54 and the final stage 58 share much in common with the second stage 56, with some major differences as follows. Unlike the second stage 56, the first stage 54 has its cathode supported from a first stage cathode input 59a, rather than from a linking structure (e.g., akin to 60) from a prior stage. The final stage includes a linking structure 64 that terminates in a last stage anode output 59c, rather than a cathode support structure (e.g., 62d of second stage 56) for a following stage. The final stage 58 is electrically insulated from vacuum enclosure 52 by dielectric insulator 53. Additionally, the relative sizes of the stages 54, 56 and 58 increase from first stage 54 to final stage 58. Finally, it should be noted that in this specification like reference numerals refer to like parts, so that, for instance, the foregoing description of anode 56a for second stage 56 applies as well to reference numeral 54a for first stage 54 and to 58a of third stage 58.

3. Method of Activating Cascaded Electron Tubes

Activation of an electron tube is the penultimate process step in the manufacture of the tube, just prior to pinching off the exhaust tubulation. The purpose of activation is to convert the as-manufactured cathode into a functioning electron emission element. Typically, this process involves drawing current from the cathode through the anode, while the tube is still connected to a vacuum pumping system. Specific implementation varies with the type of cathode used. It is important to recognize that the activation process is completely independent of the electrode geometry of the tube or tube stage.

The present invention relates to integrally series-connected electron tubes in the nature of the integral connection of the electron tubes as described above in connection with FIGS. 3 and 4. Activation of a thermionic cathode primarily changes the chemistry of the emitting surface of the cathode, while activation of a cold cathode is used to remove impurities from the cathode.

An aspect of the invention is the use of a single power supply to activate the successive stages 18a, 18b and 18c (FIGS. 3-4), as opposed to using three discrete power supplies of progressively increasing voltages. Since the cost of power high voltage power supplies increases rapidly with increasing output voltage rating, the ability to activate a very high voltage stage with a relatively low voltage power supply is desirable. This is achieved by taking advantage of the Inherent amplification provided by each stage (18a, 18b and 18c). The first stage 18a raises the voltage to the correct level to properly activate the second stage 18b; the same process is repeated for each successive stage. In the final stage (e.g., 18c or higher), the amplification process is still required but is used internally to activate that stage.

Figure 6:
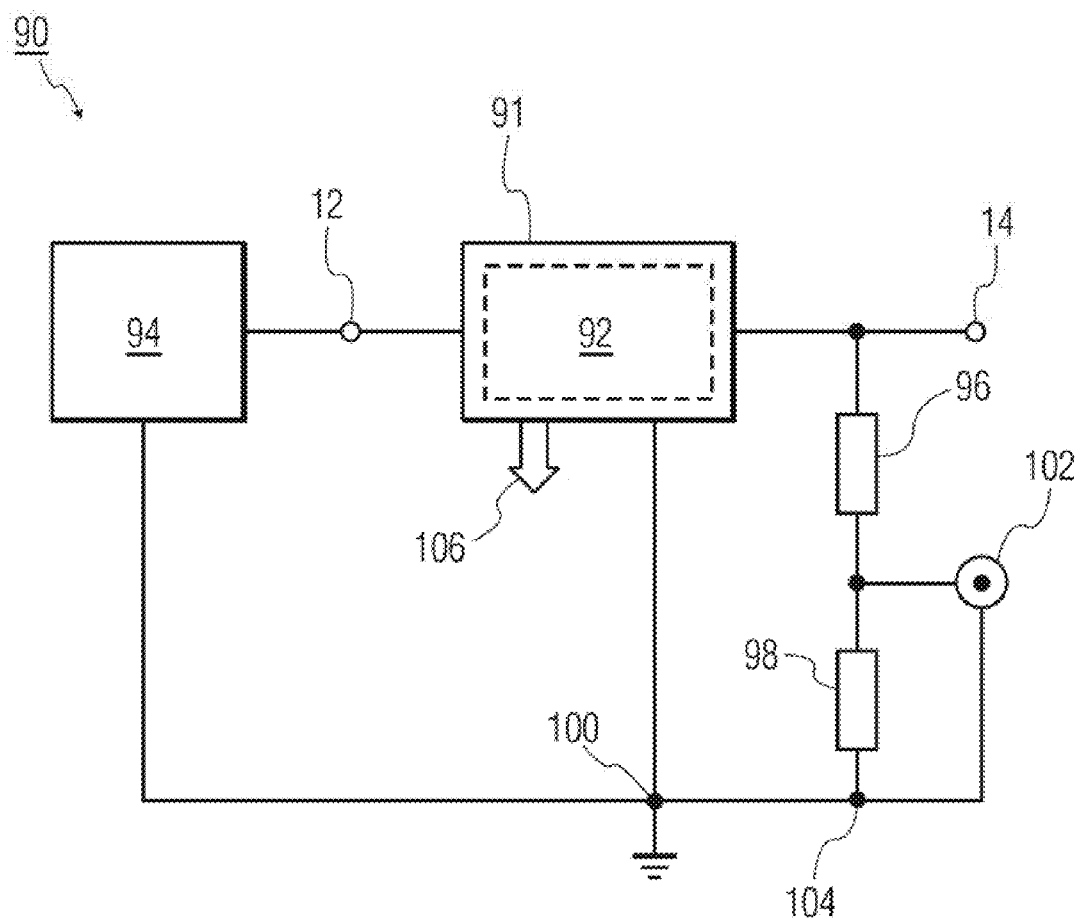
FIG. 6 is a block diagram view of a scheme for activating an integrated cascade voltage amplifier.

FIG. 6 shows a scheme 90 for activating an integrated cascade voltage amplifier (CVA) 92. Amplifier 92, shown in dashed lines within a vacuum enclosure 91, may suitably comprise the CVA described above in connection with FIGS. 3 and 4. A variable high voltage power supply 94 feeds the input terminal 12 of amplifier 92. A load resistor 96 is connected to output terminal 14 on one end, and to a shunt resistor 98 on the other end. The other side of shunt resistor 98 is connected to common ground 100. The center conductor of a coaxial jack 102 is connected to the common terminal of load resistor 96 and shunt resistor 98. The ground connection of coaxial jack 102 is connected to the shunt resistor ground connection 104. An exhaust means 106, shown diagrammatically, is used to exhaust air and impurities from vacuum enclosure 91.

To activate the CVA 92, air is exhausted from enclosure 91 by exhaust means 106. Electrical voltage from variable high voltage power supply 94 is applied between the anode and cathode of the first serially connected serially connected tube stage within CVA 92. A sufficient amount of the energy from power supply 94 is serially propagated through any intervening stage (here, the second stage) to the final stage so as to facilitate activation of all stages. Preferably, the energy supplied by the power supply 94 to the anode and cathode of the first stage is sufficient to cause activation of all stages. Beneficially, each stage amplifies the input activation voltage to the correct value for the level of activation mentioned in the preceding two sentences by virtue of its design.

Figure 7:
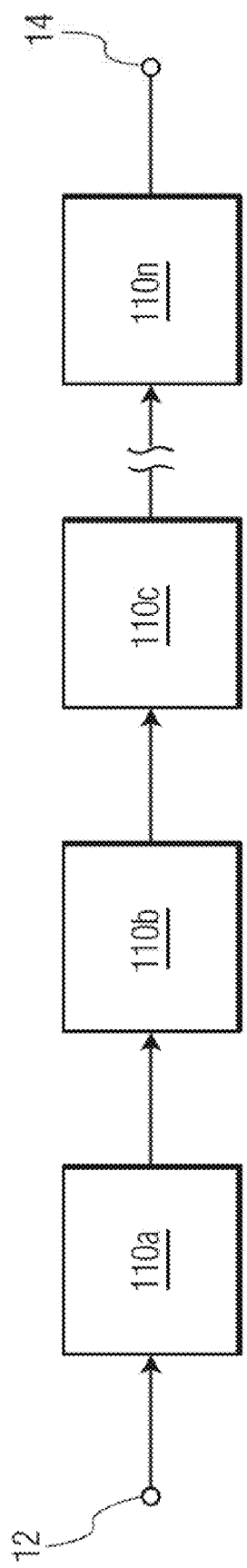
FIG. 7 is a block diagram view of a variable number of stages of a cascade voltage amplifier in accordance with the invention.

Although FIG. 6 and, by implication, FIGS. 3 and 4, show three stages of a cascade voltage amplifier (CVA), four or more stages can be incorporated into a CVA. Thus, FIG. 7 diagrammatically shows, between input 12 and output 14, stages 110a, 110b, 110c and intervening, unnumbered stages, represented by a line break, until stage 110n. These four or more stages can replace the three stages of FIGS. 3, 4 and 6. The interrelation of the various stages of FIG. 7 can be discerned from the interrelation of successive stages in FIGS. 3 and 4. In particular, stage 110a (FIG. 7) corresponds to first stage 54 (FIGS. 3 and 4), stages 110b, 110c and any further intervening stages in FIG. 7 correspond to second stage 56 in FIGS. 3 and 4, and final stage 110n of FIG. 7 corresponding to final stage 58 in FIGS. 3 and 4. The consequence of adding additional stages is a small diminution in risetime of the resulting CVA, which is governed by the risetime of the last stage and is not subject to the issue of slew rate (dv/dt).

While the invention has been described with respect to specific embodiments by way of illustration, many modifications and changes will occur to those skilled in the art.

It is, therefore, to be understood that the appended claims are intended to cover all such modifications and changes as fall within the true scope and spirit of the invention.

What is claimed is:

1. A cascade voltage amplifier for producing an amplified output in pulse or continuous wave form, comprising:
   a) at least one non-final stage comprising an electron tube configured as a switching and Class A or C amplifying means; and
   b) a final stage comprising an electron tube configured as a switching and Class A or C amplifying means; and
   c) the at least one non-final stage and the final stage being connected in series; and
   d) the amplified output having a voltage of at least 1000 volts.

2. The cascade voltage amplifier of claim 1, wherein the at least one non-final stage and the final stage are physically contained within a common vacuum enclosure.

3. The cascade voltage amplifier of claim 1, wherein the at least one non-final stage and the final stage consist of three stages.

4. The cascade voltage amplifier of claim 1, wherein the at least one non-final stage and the final stage consist of four stages.

5. The cascade voltage amplifier of claim 1, wherein:
   a) each stage includes a cylindrical outer electrode encircling at least one concentric cylindrical grid which, in turn, encircles a concentric cylindrical inner electrode;
   b) the radial spacing from the cylindrical inner electrode to the cylindrical grid is such as to create therebetween a circular waveguide supporting transverse electromagnetic mode;
   c) each non-final stage includes a linking structure for electrically joining, and being the primary mechanical support for, the outer electrode of said each non-final stage and the inner electrode of a subsequent stage; the linking structure having first and second ends and comprising:
      i. an electrical interconnection included between the first and second ends;
      ii. the first end including means for supporting the outer electrode of the foregoing stage;
      the second end including means for supporting the inner electrode of the subsequent stage; and
      iv. a common vacuum enclosure for all stages.

6. The cascade voltage amplifier of claim 5, wherein the at least one non-final stage and the final stage each includes a cold cathode field emission electron tube.

7. The cascade voltage amplifier of claim 5, wherein the linking structure of each non-final tube is an integral and gaplessly continuous structure.

8. The cascade voltage amplifier of claim 5, wherein the electrical interconnection comprises an electrical transmission line.

9. The cascade voltage amplifier of claim 5, wherein the final stage includes a linking structure for electrically joining, and being the primary mechanical support for, the outer electrode of said final stage and external circuitry; the linking structure having first and second ends and comprising:
   a) an electrical transmission line included between the first and second ends;
   b) the first end including means for supporting the outer electrode of the foregoing stage; and
   c) the second end including means for connecting to external circuitry.

10. The cascade voltage amplifier of claim 9, wherein the linking structure of each non-final stage is an integral and gaplessly continuous structure.

11. The cascade voltage amplifier of claim 5, wherein the outer electrodes are anodes and the inner electrodes are cathodes.

12. The cascade voltage amplifier of claim 5, wherein the outer electrodes are cathodes and the inner electrodes are anodes.

13. The cascade voltage amplifier of claim 5, wherein the number of non-final stages is two.

14. The cascade voltage amplifier of claim 5, wherein the number of non-final stages is three.

15. A method of activating a plurality of cascaded electron tube stages within a common vacuum enclosure, the method comprising:
   a) interconnecting the plurality of cascaded electron tube stages in series, from a non-final stage to a final stage, in such a manner that in each non-final stage an electrode is connected to an electrode of a subsequent stage by a respective electrical interconnection line;
   b) at least one of said respective electrical interconnection lines comprising a linking structure for electrically joining, and being the primary mechanical support for, an electrode of a previous stage with an electrode of a subsequent stage;
   c) placing the plurality of cascaded electron tube stages within the vacuum enclosure and exhausting air from the enclosure, and
   d) providing electrical voltage between a cathode and an anode of a first serially-connected stage so as to supply electrical energy to the first stage; a sufficient amount of said energy serially propagating through any intervening stage to the final stage so as to facilitate activation of all tube stages.

16. The method of claim 15, wherein said providing electrical voltage between the cathode and the anode of the first serially-connected stage provides sufficient energy to cause activation of all stages.

17. The method of claim 15, wherein the entire length of each linking structure forms an electrical transmission line.

18. The method of claim 15, wherein said electron tubes are cold cathode field emission electron tubes.

19. The method of claim 15, wherein the electrical interconnection line comprises an electrical transmission line.

20. The method of claim 15, wherein the plurality of cascaded electron tube stages is three in number.

21. The method of claim 15, wherein the plurality of cascaded electron tube stages is four in number.

* * * * *